United States Patent [19]

Cognion et al.

[11] Patent Number: 4,717,703

[45] Date of Patent: Jan. 5, 1988

[54] PROCESS FOR MAKING ETHYLENE OXIDE CATALYST

[75] Inventors: Jean-Marie Cognion, Saint Genis Laval; Gerard Letray, Le Havre, both of France

[73] Assignee: Atochem, France

[21] Appl. No.: 867,780

[22] Filed: May 27, 1986

[30] Foreign Application Priority Data

Apr. 11, 1986 [FR] France .................................. 86 05410

[51] Int. Cl.$^4$ .......................... B01J 21/04; B01J 23/04; B01J 23/66
[52] U.S. Cl. ..................................... 502/348; 502/347; 549/534
[58] Field of Search .................. 502/347, 348; 549/534

[56] References Cited

U.S. PATENT DOCUMENTS 4,242,235 12/1980 Cognion et al. ................. 502/348 X
4,368,144 1/1983 Mitsuhata et al. ................... 502/348

Primary Examiner—W. J. Shine
Attorney, Agent, or Firm—Sigalos & Levine

[57] ABSTRACT

A process for manufacturing silver catalysts deposited on a porous refractory support, comprising impregnating a refractory support with a portion of the silver required for the catalyst by immersing the support in a practically anhydrous solution of an organic carboxylic acid salt of silver in an organic liquid which complexes the silver ions, removing excess organic liquid from the support without causing the deposition of metallic silver thereon; depositing the remainder of the silver and at least one promoter selected from cesium, rubidium, or potassium on the support modified by the first silver deposit by immersing said modified support in a practically anhydrous solution of an organic carboxylic acid salt of silver in an organic liquid which complexes the silver ions, said organic liquid containing in the solubilized state, a salt of at least one of the promoters, before transformation of the silver deposited into metallic silver.

13 Claims, No Drawings

PROCESS FOR MAKING ETHYLENE OXIDE CATALYST

BACKGROUND OF THE INVENTION

The present invention pertains to silver catalysts intended for the manufacture of ethylene oxide by the oxidation of ethylene with molecular oxygen.

More particularly, it pertains to catalysts in which the silver is deposited on a porous refractory support which is modified by the presence of at least one promoter deposited on the said support, and to the preparation of such catalysts and their use for manufacturing ethylene oxide.

The supports used are most often formed of alumina, silica-alumina, magnesia, pumice, zirconia, clay, ceramic, natural or artificial graphite, asbestos, natural or artificial zeolite, or silicon carbide, in various forms, such as in the form of extruded parts, tablets, rings, spheres, and the like, with external dimensions most often comprised between 2 mm and 10 mm.

The preferred supports have a small specific surface, generally equaling at most 10 $m^2/g$ and an increased porosity, with the pore volume often exceeding 20% and being able to reach up to 60%.

In most cases, the specific surface is determined by the nitrogen adsorption method or BET method described by Brunauer, Emmet and Teller in *The Journal of American Chemical Society* 60, 309 (1938), while the porosity is measured by the mercury porosimetric method recommended by E. W. Washburn in *Proceedings of the National Academy of Sciences of the USA* 7, 115 (1927) and described by L. C. Darke in *Industrial and Engineering Chemistry* 41, 780 (1949) and in *Industrial and Engineering Chemistry, Analytical Edition* 17, 782 (1945).

Among the supports possessing the above-mentioned characteristics, those used most often are of the type of alumina of particularly high purity and alumina with low silica content. Alpha-alumina is particularly suitable.

The selection of such a preferred support does not suffice in itself, because the activity, the selectivity for ethylene oxide, and the long-term behavior of the catalysts are dependent not only on the support, but also on the nature of the precursors of the active constituents and the technique employed to deposit the silver and the promoters on the support.

It is a known fact that two techniques are currently in use: coating of the support with the precursors of the active phases suspended in a liquid, and impregnation of the support with the said precursors being used in a solubilized form.

It is commonly admitted at present that the second technique is more favorable than the first one, particularly because of the stronger adhesion of the active constituents.

The prior art usually qualifies the impregnation in which the silver is always accompanied with the promoter during the deposition operation as "simultaneous" impregnation, and the impregnation in which the total amount of the silver is deposited completely separated from the deposition of the promoter as "sequential" impregnation.

As is shown; for example, by U.S. Pat. Nos. 3,563,914, 3,962,136, 4,033,903, 4,010,115, 4,012,425, and 4,207,210 or Belgian Pat. No. 793,658, the sequential impregnation is practically equivalent to the simultaneous impregnation if the deposition of the promoter precedes that of the silver but is clearly inferior to it in the opposite case.

According to European Patent Application published as U.S. Pat. No. 0076504, not even the transformation of the silver deposited into metallic silver prior to the deposition of the promoter is sufficient to cause the sequential impregnation to be superior to the simultaneous impregnation.

Even though improvement of the catalysts, and even minor improvements in view of their considerable economic significance within the framework of a major industrial process for the larger-scale production of ethylene oxide, have always been a concern in industry, the total amount of the silver and the total amount of the promoter have continued to be deposited on the support according to the impregnation technique carried out either completely simultaneously or completely separately.

There was no reason to abandon this practice, because even though the two methods, simultaneous deposition and sequential deposition, are totally different from one another, they are ultimately functionally equivalent.

SUMMARY OF THE INVENTION

The catalysts according to the present invention are characterized by increased performance compared with the prior-art catalysts. They are prepared by the process according to the present invention, which is essentially distinguished from the prior-art processes involving the impregnation of the support by the fact that the total amount of the silver is not deposited either simultaneously with the promoter or separately.

The process, according to the invention, for manufacturing silver catalysts deposited on a porous refractory support, comprises impregnating a refractory support with a portion of the silver required for the catalyst by immersing the support in a practically anhydrous solution of an organic carboxylic acid salt of silver in an organic liquid which complexes the silver ions, removing excess organic liquid from the support without causing the deposition of metallic silver thereon; depositing the remainder of the silver and at least one promoter selected from cesium, rubidium, or potassium on the support modified by the first silver deposit, by immersing said modified support in a practically anhydrous solution of an organic carboxylic acid salt of silver in an organic liquid which complexes, the silver ions, said organic liquid containing, in the solubilized state, a salt of at least one of the promoters, before transformation of the silver deposited into metallic silver.

The invention also comprises the resultant catalyst and the process of making ethylene oxide utilizing such catalyst.

DETAILED DESCRIPTION

In preparing the catalyst, the quantity of silver in the catalyst may vary within broad limits, e.g., between about 5 and 20 wt.%, and preferably between 8 and 16 wt.%.

The silver present in the catalyst originates from precursors, salts of aliphatic or aromatic acids such as silver acetate or silver benzoate, which are used directly or are formed within the organic liquid from silver oxide and acid.

The quantity of silver deposited during the impregnation of the support modified by the first silver deposit is preferably most often between about 25% and 75% of the total quantity of silver to be deposited.

The quantity of promoter (cesium, rubidium, and/or potassium) deposited, expressed as metal in the catalyst, may also vary within broad limits, being most often between 0.005 and 0.05 wt.%, and preferably between 0.01 and 0.03 wt.%.

The promoter may be used directly in the form of a salt preferably acetate, chloride, nitrate, or in the form of an oxide transformed into a salt in the organic liquid by the action of the acid selected.

Heterocyclic compounds containing three carbon atoms, one oxygen atom and one nitrogen atom, as recommended by European Patent Application published as U.S. Pat. No. 0005388, and particularly oxazole, methyl-2-oxazoline-2 or, ethyl-2-oxazoline-2, are the preferred of the organic liquids used to form the impregnating solutions.

The compounds principally or exclusively consisting of a $\alpha$-alumina, having a specific surface between 0.1 m$^2$/g and 5 m$^2$/g, preferably below 1 m$^2$/g, and a pore volume between 20% and 50% are undeniably the best of the preferred supports mentioned above in the Background of the Invention as suitable for use with silver.

Before each impregnation, the product to be impregnated is degassed at a temperature that is preferably between about 50° C. and 100° C. under an absolute pressure not exceeding ca. $25 \times 10^{-3}$ bar during a period which is between ca. 0.5 and five hours under these conditions.

The impregnations may be carried out according to any known technique which permits complete immersion of the solid to be impregnated either statically or dynamically by circulating the impregnating solution at a temperature which is most often between about 20° C. and 60° C. during times ranging from ca. 0.25 to two hours.

After the first impregnation of the support, the excess organic liquid is preferably removed by heating the impregnated support, which was allowed to dry at a temperature equaling at most 100° C. under a nitrogen stream flowing at a rate of and including, per kilogram, 5 l/hour and 0.5 m$^3$/hour, and the duration of the operation does not generally exceed 24 hours.

An operation analogous to the above-described one may also be carried out, if desired, after the second impregnation.

The final formation of metallic silver is preferably carried out by heat treatment of the support modified by the consecutive deposits of silver, on one hand, and of silver and promoter, on the other hand.

A particularly suitable heat treatment consists of first bringing the solid to be treated in a nitrogen stream flowing at rates between 5 l/hour and 0.5 m$^3$/hour per kg to a temperature between ca. 150° C. and 300° C., reached at a rate of temperature rise preferably equaling at most 50° C./hour, during a time equaling at least the time needed to practically achieve cessation of weight loss, of subsequently cooling in a nitrogen stream to a temperature equaling at most ca. 100° C. and finally bringing the temperature preferably to between 150° C. and 200° C., reached at a rate preferably between 50° C./hour and 100° C./hour in an air current flowing at a rate preferably between 5 l/hour and 0.5 m$^3$/hour per kg, during the time needed for the formation of carbon dioxide to practically cease.

The catalysts according to the present invention characterized in that they are obtained according to the above-described mode of preparation, have the advantage of leading to improved results compared with those achieved with the known catalysts obtained by the prior-art processes involving impregnation, if they are used in the process of manufacturing ethylene oxide, which is amply described, e.g., in *Revue de l'Institut Francais du Petrole* 11(4), 490–500 or more recently in *Chemical Engineering Process*, 75(1), 67–72 (1979).

The invention will be further described in connected with the following examples which are set forth for purposes of illustration only.

EXAMPLE 1

This example illustrates the preparation of catalysts according to the present invention; A-1, A-2, A-3, A-4, A-5, B-1, and the catalysts manufactured for comparison according to a known "simultaneous" impregnation process, catalysts AC-1 and AC-2.

The percentages indicated in this and the following examples are weight percentages.

50 g of a support A formed by practically pure SAHT type $\alpha$-alumina with a specific surface smaller than 1 m$^2$/g, manufactured by the firm of Union Catalysts Inc. in the form of extruded rings with an outside diameter of 6.4 mm, an inside diameter of 3.2 mm and a length of 7 to 8 mm, in degassed for two hours at 50° C. under an absolute pressure of $25 \times 10^{-3}$ bar and then impregnated by total immersion into a solution of silver acetate in ethyl-2-oxazoline-2 containing 24% silver acetate at 40° C. for 30 minutes.

The support thus impregnated is treated at a temperature of 90° C. for 18 hours in a nitrogen stream flowing at a rate of 5 l/hour before being degassed at 80° C. for two hours under an absolute pressure of $25 \times 10^{-3}$ bar and before being subjected to a subsequent impregnation, for 30 minutes at 40° C., by complete immersion into a solution of silver acetate in ethyl-2-oxazoline-2 containing 24% silver acetate and a quantity of cesium acetate necessary to obtain a catalyst containing 0.03% cesium.

A treatment is carried out under nitrogen at 90° C., which is identical with that following the first impregnation.

The solid obtained is treated for 18 hours in nitrogen flowing at a rate of 7.5 l/hour at a temperature of 270° C., reached at a rate of temperature rise of 20° C./hour and then cooled to 80° C. before being treated with air flowing at a rate of 7.5 l/hour for 48 hours at a temperature of 175° C., which is reached within one hour.

Catalyst A-1 thus obtained contains 0.03% cesium and 9% silver, 25% of the silver being deposited with the cesium.

According to the same procedure as that applied in the case of A-1, a catalyst A-2 is prepared by depositing a first silver deposit by immersion of support A into a solution of silver acetate in pyridine, containing 35% silver acetate and depositing the rest of the silver and the promoter by immersion in a silver acetate solution in pyridine containing 35% silver acetate and the amount of cesium acetate needed to obtain a catalyst containing 0.015% cesium.

Catalyst A-2 thus contains 14.5% silver and 0.015% cesium.

According to the same procedure as that used for A-1, but with an impregnating solution containing the rest of the silver and the cesium, which contains 40% silver acetate, the catalysts A-3 and A-4 are prepared; both of them contain 13% silver and 0.01% and 0.03% cesium, respectively. In the case of A-3 as well as A-4, the rest of the silver deposited together with the cesium corresponds to 60% of the total quantity of the silver deposited.

According to the same procedure as that used for the following catalysts, but depositing silver alone by immersion of the support in a silver benzoate solution by oxazole containing 31% silver benzoate and depositing the rest of the silver, which amounts to 60% of the total amount of silver finally deposited as well as the cesium by immersion of the support modified by the first silver deposit into a silver benzoate solution in oxazole containing 55% silver benzoate and the quantity of cesium acetate necessary to obtain a catalyst containing 0.025% cesium, a catalyst A-5 is prepared, which contains 14.5% silver along with 0.025% cesium.

A support B, which differs from support A only by its length not exceeding 3 to 4 mm, is used to manufacture the catalyst B-1 in the same manner as catalyst A-4. Just as A-4, B-1 contains 13% silver and 0.03% cesium.

Catalyst AC-1 was prepared according to a known technique; after degassing support A, by "simultaneous" inpregnation of the said support by immersion into a solution of silver acetate in ethyl-2-oxazoline-2, containing 32% silver acetate and the quantity of cesium acetate permitting a catalyst containing 0.032% cesium to be prepared.

After elimination of the excess ethyl-2-oxazoline-2 as was described in connection with the other catalysts, the support, on which the total amount of the silver and the total amount of the cesium were thus deposited, is treated to transform the silver deposited into metallic silver as described in connection with the catalysts according to the present invention.

Catalyst AC-1 contains 9.2% silver, which permits its comparison with A-1.

Catalyst AC-2 was prepared by treating support A according to the technique used for the catalysts according to the present invention, with the essential difference that the promoter accompanied the silver during the first as well as the second impregnation, each of which was carried out by immersion into a silver acetate solution in pyridine containing 35% silver acetate and each time an equal quantity of cesium acetate. Catalyst AC-2 contains 14.3% silver and 0.015% cesium and can consequently be compared with A-2.

EXAMPLE 2

This example illustrates the utilization of the catalysts according to the present invention and, for comparison, of the prior-art catalysts in connection with the manufacture of ethylene oxide.

In all the experiments reported in this example, 40 g catalyst are charged into a glass reactor with a diameter of 25 mm, which is heated by external hot air circulation, above a bed of glass spheres serving to preheat the gaseous mixture of the reagents entering from the bottom of the reactor at a rate of 20 l/hour at 20° C. and under atmospheric pressure at which the experiments are carried out.

The mixture of the reagents has the following volumetric composition:

| | |
|---|---|
| ethylene | 17.5% |
| oxygen | 7.0% |

-continued

| | |
|---|---|
| ethane | 1.0% |
| carbon dioxide | 6.0% |
| monomeric vinyl chloride | $1.5 \times 10^{-4}\%$ |
| The rest to 100% is nitrogen. | |

The selectivity of the reaction with respect to ethylene oxide, designated by S, is expressed, in %, by the number of moles of ethylene oxide formed relative to the number of moles of ethylene oxide transformed.

The results of the experiments carried out are shown in Table I below, which also indicates, for each value of S, the charge C, which is defined as the ethylene oxide concentration in vol.% in the gaseous mixture leaving the reactor.

TABLE I

| Catalyst | Temperature °C. | C | S |
|---|---|---|---|
| A-1 | 180 | 1 | 82 |
|  | 205 | 1.5 | 82 |
| AC-1 | 205 | traces |  |
|  | 230 | 1 | 82 |
| A-2 | 183 | 1 | 82 |
| AC-2 | 183 | 1 | 80.5 |
| A-3 | 190 | 1 | 80.5 |
| A-4 | 180 | 1 | 82 |
|  | 194 | 1.8 | 80.5 |
| A-5 | 186 | 1 | 81 |
|  | 191 | 1.8 | 80 |
| B-1 | 200 | 1 | 85 |
|  | 212 | 1.5 | 84 |

EXAMPLE 3

46.5 g catalyst B-1 are charged into the reactor of Example 2 and tested under the following conditions: the gaseous reagent mixture enters the reactor at a rate of 25 l/hour measured as in Example 2 and with the same volumetric composition as in that example, with the exception that the rest to 100% is methane instead of nitrogen.

The results obtained are shown in Table II, C and S have the same meanings as in Example 2.

TABLE II

| Temperature °C. | C | S |
|---|---|---|
| 196 | 0.8 | 84 |
| 199 | 1.6 | 82 |

It is apparent from Tables I and II that the catalysts prepared by the process according to the present invention represent a considerable improvement compared with the known range and permit, in particular, a high selectivity to be maintained if the ethylene oxide leaving the reactor is increased, and a high degree of reliability of operation, and the above-mentioned qualities, are achieved at a low temperature.

The replacement of the oxazole or ethyl-2-oxazoline-2 by a different compound of the same nature, such as methyl-2-oxazoline-2 for preparing the catalysts according to the present invention has no appreciable influence.

The improvement due to the present invention is also present if cesium is used alone or is partially or completely replaced by potassium and/or rubidium.

While the invention has been described in connection with a preferred embodiment, it is not intended to limit the scope of the invention to the particular form set forth, but, on the contrary, it is intended to cover such alternatives, modifications, and equivalents as may be included within the spirt and scope of the invention as defined by the appended claims.

What is claimed is:

1. A process for manufacturing silver catalysts deposited on a porous refractory support, comprising impregnating a refractory support with a portion of the silver required for the catalyst by immersing the support in a substantially anhydrous solution of an organic carboxylic acid salt of silver in an organic liquid which complexes the silver ions, removing excess organic liquid from the support without causing the deposition of metallic silver thereon by heating same at a temperature equaling at most 100° C.; depositing the remainder of the silver and at least one promoter selected from cesium, rubidium, or potassium on the support modified by the first organic carboxylic salt of silver deposit by immersing said modified support in a practically anhydrous solution of an organic carboxylic acid salt of silver in an organic liquid which complexes the silver ions, said organic liquid containing, in the solubilized state, a salt of at least one of the promoters, before transformation of the silver deposited into metallic silver.

2. The process of claim 1, wherein the rest of the silver deposited is between about 25% and 75% of the total quantity of silver deposited.

3. The process of claim 1, wherein the total quantity of silver deposited is between 5 and 20 wt.% of the catalyst.

4. The process of claim 3, wherein the total quantity of silver deposited is between 8 and 16 wt.% of the catalyst.

5. The process of claim 4, wherein the silver salt is selected from silver acetate or silver benzoate.

6. The process of claim 5, wherein the quantity of promoter deposited, expressed as the metal, is between 0.005 and 0.05 wt.% of the catalyst.

7. The process of claim 6, wherein the quantity of promoter deposited is between 0.01 and 0.03 wt.% of the catalyst.

8. The process of claim 7, wherein the promoter salt is an acetate, chloride, or nitrate salt.

9. The process of claim 8, wherein the organic liquid complexing the silver ions is selected from pyridine, oxazole, methyl-2-oxazoline-2, or ethyl-2-oxazoline-2.

10. The process of claim 9, wherein the excess organic liquid is removed from the impregnated support by heating same at a temperature equaling at most 100° C. in a nitrogen stream.

11. The process of claim 10, wherein after removal of the excess organic liquid, the support modified by the first silver deposit is degassed prior to the deposition of the rest of the silver and of the promoter under an absolute pressure of at most $25 \times 10^{-3}$ bar and at a temperature between about 50° C. and 100° C.

12. The process of any one of claims 1 to 11, wherein the metallic silver is formed by heat treatment of the support modified by the deposition of a portion of the silver followed by the deposition of the remainder of the silver and promoter, first in a nitrogen stream at a temperature between 150° C. and 300° C. for a time at least equaling the time necessary for weight loss to practically stop and then in an air stream at a temperature between 150° C. and 200° C. for a time at least equaling the time needed for the carbon dioxide formation to practically cease.

13. The process of any one of claims 1 to 11, wherein the support is a practically pure α-alumina with a specific surface smaller than 1 m²/g.

* * * * *

UNITED STATES PATENT AND TRADEMARK OFFICE
CERTIFICATE OF CORRECTION

PATENT NO. : 4,717,703
DATED : January 5, 1988
INVENTOR(S) : Cognion et al

It is certified that error appears in the above-identified patent and that said Letters Patent are hereby corrected as shown below:

Column 2, line 5, "U.S. Pat." should be deleted;

Column 4, line 28, cancel "in" and substitute therefor --is--;

Column 7, line 2, correct "spirt" to read --spirit--.

Signed and Sealed this

Fourth Day of October, 1988

*Attest:*

DONALD J. QUIGG

*Attesting Officer*        *Commissioner of Patents and Trademarks*